United States Patent
Cho et al.

(10) Patent No.: US 8,658,769 B2
(45) Date of Patent: Feb. 25, 2014

(54) DIAGNOSTIC MARKER FOR HEPATOCELLULAR CARCINOMA COMPRISING ANTI-FASN AUTOANTIBODIES AND A DIAGNOSTIC COMPOSITION FOR HEPATOCELLULAR CARCINOMA COMPRISING ANTIGENS THEREOF

(75) Inventors: Eun Wie Cho, Daejon (KR); Chang Kyu Heo, Daejeon (KR); Mi Kyung Woo, Daejeon (KR); Hai Min Hwang, Daejeon (KR); Hyang Sook Yoo, Daejeon (KR); Jeong Heun Ko, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/501,426

(22) PCT Filed: Oct. 1, 2010

(86) PCT No.: PCT/KR2010/006727
§ 371 (c)(1),
(2), (4) Date: Apr. 11, 2012

(87) PCT Pub. No.: WO2011/046309
PCT Pub. Date: Apr. 21, 2011

(65) Prior Publication Data
US 2012/0264147 A1 Oct. 18, 2012

(30) Foreign Application Priority Data

Oct. 12, 2009 (KR) .................. 10-2009-0096991
Feb. 26, 2010 (KR) .................. 10-2010-0018205

(51) Int. Cl.
*C07K 16/00* (2006.01)
(52) U.S. Cl.
USPC .................................. 530/387.1; 530/388.2
(58) Field of Classification Search
None
See application file for complete search history.

(56) References Cited

U.S. PATENT DOCUMENTS

| 5,864,011 A * | 1/1999 | Kuhajda et al. ............... 530/324 |
| 2002/0103212 A1 | 8/2002 | Serizawa et al. |
| 2004/0024050 A1 | 2/2004 | Smith et al. |
| 2007/0142456 A1 | 6/2007 | Kuhajda et al. |
| 2008/0254481 A1 * | 10/2008 | Love et al. ...................... 435/7.1 |
| 2009/0162870 A1 | 6/2009 | Medghalchi et al. |

FOREIGN PATENT DOCUMENTS

| KR | 1020080106157 A | 12/2008 |
| KR | 1020090029338 A | 3/2009 |

OTHER PUBLICATIONS

Paul, Fundamental Immunology, 3rd Edition, 1993, pp. 292-295.*
Rudikoff et al, Proc. Natl. Acad. Sci. USA 1982, vol. 79: p. 1979.*
Casset et al, BBRC 307, 198-205, 2003.*
Pascalis et al The Journal of Immunology vol. 169, 3076-3084, 2002.*
Wang et al., "Universal PCR amplification of mouse immunoglobulin gene variable regions: the design of degenerate primers and an assessment of the effect of DNA polymerase 3X to 5X exonuclease activity." J. Immunological Methods 2000, 233:167-177.
Ho et al., "Fatty acid synthase inhibitors cerulenin and C75 retard growth and induce caspase-dependent apoptosis in human melanoma A-375 cells." Biomedicine & Pharmacotherapy 2007, 61:578-587.
Leifeld et al., "Anti-Apoptotic Function of Gelsolin in Fas Antibody-Induced Liver Failure in Vivo." American Journal of Pathology 2006, 168(3):778-785.

* cited by examiner

*Primary Examiner* — Lei Yao
(74) *Attorney, Agent, or Firm* — Tanya A. Arenson; Casimir Jones, S.C.

(57) ABSTRACT

The present invention relates to an autoantibody specifically recognizing the epitope sequence of FASN (fatty acid synthase), more particularly, to the autoantibody or a fragment comprising an antigen-binding site thereof, a diagnostic composition for hepatocellular carcinoma comprising an agent capable of assessing the expression level of the autoantibody, a hybridoma cell line producing the autoantibody, a diagnostic kit for hepatocellular carcinoma comprising the composition, a method for detecting the autoantibody of hepatocellular carcinoma patient using the composition, and a method for screening a therapeutic agent for hepatocellular carcinoma by administering candidate materials for hepatocellular carcinoma treatment to confirm a reduction in the expression level of autoantibody.

7 Claims, 11 Drawing Sheets

Figure 5

| Clone number | Peptide sequence | SEQ ID NO. |
|---|---|---|
| K1-p3 | CRMSRRSNC | 28 |
| K1-p7 | CMRNPKRC | 29 |
| K1-p22 | CRRRLNRTC | 30 |
| K1-p33 | CRMRIRRNC | 31 |
| K1-p34 | CHPHPRPRC | 32 |

Figure 7

| SEQ ID NO. | Gene_Symbol=Fasn Fatty acid synthase | | Mass: 272257 | Score: 80 | Queries matched: 4 |
|---|---|---|---|---|---|
| | Query | Peptide | Score | Sequence within mouse FASN NP_032014 (1..2504) | |
| 33 | 1 | R.LKEDTQVADVTTSR.C | 80 | 1069-1084 | |
| 34 | 2 | R.AKMTPGCEAEAEAEALCFFIK.Q | 13 | 2345-2367 | |
| 35 | 3 | K.LGMLSPDGTCRSFDDSGSGYCR.S | 12 | 202-225 | |
| 36 | 4 | R.GQCIKDAHLPPGSMAAVGLSWEECK.Q | 6 | 606-632 | |

Figure 10

(SEQ ID NOS.: 20-21)

K1-V$_H$

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| Q/E | V | Q/K | L | Q/E | Q | S | G | A | E | L | A | R | P | G |
| SAR | GTM | MAG | CTG | SAG | CAG | TCW | GGA | GCT | GAG | CTG | GCG | AGG | CCT | GGG |

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| A | S | V | K | L | S | C | K | A | S | G | Y | T | F | T |
| GCT | TCA | GTG | AAG | CTG | TCC | TGC | AAG | GCT | TCT | GGC | TAC | ACC | TTC | ACA |

----------CDR1----------

| 31 | 32 | 33 | 34 | 35 | 36 | 37 | 38 | 39 | 40 | 41 | 42 | 43 | 44 | 45 |
|----|----|----|----|----|----|----|----|----|----|----|----|----|----|----|
| S | Y | G | I | S | W | V | K | Q | R | T | G | Q | G | L |
| AGC | TAT | GGT | ATA | AGC | TGG | GTG | AAG | CAG | AGA | ACT | GGA | CAG | GGC | CTT |

-----------------CDR2-----------------

| 46 | 47 | 48 | 49 | 50 | 51 | 52 | 53 | 54 | 55 | 56 | 57 | 58 | 59 | 60 |
|----|----|----|----|----|----|----|----|----|----|----|----|----|----|----|
| E | W | I | G | E | I | Y | P | R | S | G | N | T | Y | Y |
| GAG | TGG | ATT | GGA | GAG | ATT | TAT | CCT | AGA | AGT | GGT | AAT | ACT | TAC | TAC |

| 61 | 62 | 63 | 64 | 65 | 66 | 67 | 68 | 69 | 70 | 71 | 72 | 73 | 74 | 75 |
|----|----|----|----|----|----|----|----|----|----|----|----|----|----|----|
| N | E | K | F | K | G | K | A | T | L | T | A | D | K | S |
| AAT | GAG | AAG | TTC | AAG | GGC | AAG | GCC | ACA | CTG | ACT | GCA | GAC | AAA | TCC |

| 76 | 77 | 78 | 79 | 80 | 81 | 82 | 83 | 84 | 85 | 86 | 87 | 88 | 89 | 90 |
|----|----|----|----|----|----|----|----|----|----|----|----|----|----|----|
| S | S | T | A | Y | M | E | L | R | S | L | T | S | E | D |
| TCC | AGC | ACA | GCG | TAC | ATG | GAG | CTC | CGC | AGC | CTG | ACA | TCT | GAG | GAC |

-----------CDR3-----------

| 91 | 92 | 93 | 94 | 95 | 96 | 97 | 98 | 99 | 100 | 101 | 102 | 103 | 104 | 105 |
|----|----|----|----|----|----|----|----|----|-----|-----|-----|-----|-----|-----|
| S | A | V | Y | F | C | A | R | V | Y | Y | Y | G | S | S |
| TCT | GCG | GTC | TAT | TTC | TGT | GCA | AGG | GTT | TAT | TAC | TAC | GGT | AGT | AGC |

| 106 | 107 | 108 | 109 | 110 | 111 | 112 | 113 | 114 | 115 | 116 | 117 | 118 | 119 | 120 |
|-----|-----|-----|-----|-----|-----|-----|-----|-----|-----|-----|-----|-----|-----|-----|
| Y | G | Y | W | G | Q | G | T | T | L | T | V | S | S | E |
| TAC | GGC | TAC | TGG | GGC | CAA | GGC | ACC | ACT | CTC | ACA | GTC | TCC | TCA | GAG |

| 121 | 122 | 123 | 124 | 125 | 126 | 127 |
|-----|-----|-----|-----|-----|-----|-----|
| S | Q | S | F | P | N | V |
| AGT | CAG | TCC | TTC | CCA | AAT | GTC |

Figure 11

(SEQ ID NOS.: 22-23)

K1-V_L

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| D | I | V | L/I | T | Q | T/S | P | L | T | L | S | V | T | I |
| GAY | ATT | GTG | MTC | ACA | CAR | WCT | CCA | CTC | ACT | TTG | TCG | GTT | ACC | ATT |

---------------------------------------------------CDR1---

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| G | Q | P | A | S | I | S | C | K | S | S | Q | S | L | L |
| GGA | CAA | CCA | GCC | TCC | ATC | TCT | TGC | AAG | TCA | AGT | CAG | AGC | CTC | TTA |

| 31 | 32 | 33 | 34 | 35 | 36 | 37 | 38 | 39 | 40 | 41 | 42 | 43 | 44 | 45 |
|----|----|----|----|----|----|----|----|----|----|----|----|----|----|----|
| D | S | D | G | K | T | Y | L | N | W | L | L | Q | R | P |
| GAT | AGT | GAT | GGA | AAG | ACA | TAT | TTG | AAT | TGG | TTG | TTA | CAG | AGG | CCA |

---------------------------------------------------CDR2---

| 46 | 47 | 48 | 49 | 50 | 51 | 52 | 53 | 54 | 55 | 56 | 57 | 58 | 59 | 60 |
|----|----|----|----|----|----|----|----|----|----|----|----|----|----|----|
| G | Q | S | P | K | R | L | I | Y | L | V | S | K | L | D |
| GGC | CAG | TCT | CCA | AAG | CGC | CTA | ATC | TAT | CTG | GTG | TCT | AAA | CTG | GAC |

| 61 | 62 | 63 | 64 | 65 | 66 | 67 | 68 | 69 | 70 | 71 | 72 | 73 | 74 | 75 |
|----|----|----|----|----|----|----|----|----|----|----|----|----|----|----|
| S | G | V | P | D | R | F | T | G | S | G | S | G | T | D |
| TCT | GGA | GTC | CCT | GAC | AGG | TTC | ACT | GGC | AGT | GGA | TCA | GGG | ACA | GAT |

| 76 | 77 | 78 | 79 | 80 | 81 | 82 | 83 | 84 | 85 | 86 | 87 | 88 | 89 | 90 |
|----|----|----|----|----|----|----|----|----|----|----|----|----|----|----|
| F | T | L | K | I | S | R | V | E | A | E | D | L | G | V |
| TTC | ACA | CTG | AAA | ATC | AGC | AGA | GTG | GAG | GCT | GAG | GAT | TTG | GGA | GTT |

---------------------------------------------------CDR3---

| 91 | 92 | 93 | 94 | 95 | 96 | 97 | 98 | 99 | 100 | 101 | 102 | 103 | 104 | 105 |
|----|----|----|----|----|----|----|----|----|-----|-----|-----|-----|-----|-----|
| Y | Y | C | W | Q | G | T | H | F | P | R | T | F | G | G |
| TAT | TAT | TGC | TGG | CAA | GGT | ACA | CAT | TTT | CCT | CGG | ACG | TTC | GGT | GGA |

| 106 | 107 | 108 | 109 | 110 | 111 | 112 | 113 | 114 | 115 | 116 | 117 | 118 | 119 | 120 |
|-----|-----|-----|-----|-----|-----|-----|-----|-----|-----|-----|-----|-----|-----|-----|
| G | T | K | L | E | I | K | R | A | D | A | A | P | T | V |
| GGC | ACC | AAG | CTG | GAA | ATC | AAA | CGG | GCT | GAT | GCT | GCA | CCA | ACT | GTA |

| 121 |
|-----|
| S |
| TCC |

DIAGNOSTIC MARKER FOR HEPATOCELLULAR CARCINOMA COMPRISING ANTI-FASN AUTOANTIBODIES AND A DIAGNOSTIC COMPOSITION FOR HEPATOCELLULAR CARCINOMA COMPRISING ANTIGENS THEREOF

TECHNICAL FIELD

The present invention relates to a diagnostic method for hepatocellular carcinoma comprising an agent capable of assessing the expression level of anti-FASN autoantibody, more particularly, to a diagnostic composition for hepatocellular carcinoma comprising an agent capable of assessing the expression level of the autoantibody, a hybridoma cell line producing the autoantibody, a diagnostic kit for hepatocellular carcinoma comprising the composition, a method for detecting the autoantibody of hepatocellular carcinoma patient using the composition, and a method for screening a therapeutic agent for hepatocellular carcinoma by administering candidate materials for hepatocellular carcinoma treatment to confirm a reduction in the expression level of the autoantibody.

BACKGROUND ART

Liver diseases including hepatitis, liver cirrhosis, hepatocellular carcinoma or the like are the most common diseases in Korea, Japan, Taiwan, China, and most of Southeast Asian countries. Among cancer-related deaths, hepatocellular carcinoma is the fourth leading cause of death worldwide (five hundred and five thousand people) (World Health Organization, 1997). In Korea, the incidence of hepatocellular carcinoma ranks third (11.5%) among causes of cancer (Cancer Incidence in Korea, 2002).

To date, a tissue biopsy has been performed or a marker protein of hepatocellular carcinoma such as AFP has been examined for the diagnosis of hepatocellular carcinoma. In addition, several biomarkers have been suggested for the diagnosis, prognosis, or evaluation of treatment efficacy. Among them, AFP and PIVKA-II are the most well-known biomarkers. However, there is still a weak point in their specificity and sensitivity. With recent advances in genomics and proteomics, several candidate proteins and genes as hepatocellular carcinoma markers have been reported. However, the reported genes are mainly used to target the tissue, and there is still no evidence for their secretion to the blood and feasibility of using as serological diagnostic markers. This is because that due to intrinsic properties of biomarkers, most of the studies on tumor markers have focused on their expression differences in the tissue, and their high expression in the tissue does not indicate their availability as diagnostic markers in the urine or serum. Therefore, for convenient diagnosis, it is important to discover tumor markers found in the blood or urine, and there is a need to analyze biomarkers by methods different from previous approaches and develop a diagnostic method for liver diseases including hepatocellular carcinoma.

To solve the above problems, a plurality of tumor markers have been discovered from the blood, tissue, or discharge, but many tumor markers are detected or their expression increased even though cancer development is not observed. Therefore, these markers used for cancer diagnosis are only incidental tools and have not become independent diagnostic tools.

Meanwhile, at the early stage of development, an individual has an immune system which is unique in its ability to distinguish between self and non-self molecules, whereby antigen-antibody reaction (humoral immune response) and cellular immune response are normally induced in response to only foreign antigens exposed to the immune system. However, production of antibodies against self-antigens is observed in certain diseases. In this case, localization of antigen expression is different from that in normal cells, leading to secretion of the intracellular proteins from the cell, or the antigens undergo a conformational change or other abnormal properties are manifested. In regard to cancer, since the 1970s, it has been reported that abnormal growth of cancer cells is accompanied by production of autoantibodies against antigens derived from cancer cells, and these antigens are called as tumor-associated antigens(TAA). Until now, a variety of tumor-associated antigens have been discovered. Among them, HER-2/neu oncoprotein was reported to be a receptor protein located on the cell membrane and induce autoantibodies. A tumor suppressor protein p53 was also reported to induce autoantibodies. In addition, cell proliferation-associated proteins, cyclin B1 and CENP-F (centromere protein F), and onconeurological proteins, Hu and Yo were also known to induce autoantibodies. Taken together, it is inferred that many more autoantibodies against tumor-associated antigens exist, and many trials have attempted to screen tumor-associated autoantibodies in a large scale.

To identify autoantibodies, SEREX (selological analysis of recombinant cDNA expression libraries of human tumors with autologous serum) has been conventionally utilized, by which autoantibodies are detected by selological analysis of protein expression libraries of human tumors with the blood of a cancer patient. However, this method has a limitation in the preparation of diverse expression libraries of tumor-derived proteins. In addition, since final products of the proteins undergo various posttranslational modifications (PTM) after transcription, if it is not considered, protein expression libraries are not sufficient for the detection of autoantigens.

Alternatively, recent advances in the field of proteomics have lead to the identification of autoantibodies. In proteomic technologies, tumor-derived proteins are separated in 2D-PAGE, protein spots are visualized showing a reactivity to the blood plasma of cancer patients as an autoantibody sample, and then the proteins are identified by mass spectrometry. This method is also called SERPA (serological proteome analysis). MAPPing (Multiple affinity protein profiling) is also employed, in which an affinity chromatography resin conjugated with antibodies isolated from the patient's blood is prepared, tumor cell-derived proteins are applied thereto, and bound proteins are identified by mass spectrometry. In another method, a protein chip is manufactured by separation of tumor cell lysate into several thousand fractions, and then the reactivity of a patient's blood thereto is analyzed to detect autoantibodies.

These proteomic technologies have the advantage of directly analyzing the antibody reactivity to tumor cell-derived proteins retaining PTM properties, thereby detecting various autoantibodies, which could not be detected by SEREX. However, these proteomic technologies also have drawbacks.

One is a quantitative problem of antibodies. If the subject to be analyzed is a mixture of two or more, one of them, of which the quantity is greater than those of the others, is dominantly analyzed, and thus the others may be excluded from the analysis. The serum of a patient is a mixture of numerous autoantibodies, and thus the analytical range is determined by differences in their quantity and affinity to antigens, resulting in the failure of analysis of the desired autoantibody. Another problem is that patient-dependency on an autoantibody to be analyzed impairs a systematic analysis on the production of autoantibody in cancer development. In addition, it is very hard to collect an excessive amount of blood from a patient, and therefore, further studies cannot be conducted. The other problem is the conservation of the epitope recognized by an antibody. In accordance with current immunological knowledge, the epitope of an antibody can be divided into two types: a protein sequence-dependent epitope (sequential epitope) and a protein structure-dependent epitope (conformational epitope). In vivo, induction of antibodies against specific antigens is influenced by the physical state of the antigen primarily reacted with the antibody, which indicates that an antigen-antibody reaction occurs in a solution state and the antigen protein maintains its conformation dissolved in the blood. Therefore, upon analysis of antibody-antigen reaction in ex vivo, it is preferably performed in a solution state because their binding is well maintained in the solution. In the above mentioned SERPA, 2D electrophoresis is performed for analysis of the protein mixed solution, in which proteins to be analyzed are denatured using SDS and urea, and the linearized proteins are reacted with antibodies. Thus, if the epitope is a sequential epitope, the antibody-antigen reaction can be detected, but if the epitope is a conformational epitope, the antibody-antigen reaction cannot be detected.

DISCLOSURE

Technical Problem

The aforementioned studies on autoantibodies have reported their availability as tumor markers, but their diagnostic effects are not satisfactory. The autoantibodies still have limitations as a biomarker for cancer diagnosis, and the detection method of autoantibodies also have limitations in that it does not contain many cases or requires excessive experiments. Thus, there are still difficulties in the development of autoantibody markers for the diagnosis of hepatocellular carcinoma.

Therefore, the present inventors have developed an effective identification method for autoantibodies, and they investigated an autoantibody that is significantly increased in hepatocellular carcinoma by using the method, completing the present invention.

Technical Solution

It is an object of the present invention to provide an autoantibody recognizing FASN (fatty acid synthase) or a fragment comprising an antigen-binding site thereof.

It is another object of the present invention to provide a diagnostic composition for hepatocellular carcinoma, comprising an agent capable of assessing the expression level of anti-FASN autoantibody.

It is still another object of the present invention to provide a hybridoma cell line producing anti-FASN autoantibody.

It is still another object of the present invention to provide a diagnostic kit for a hepatocellular carcinoma, comprising an antigen which specifically binds to anti-FASN autoantibody.

It is still another object of the present invention to provide a method for detecting the anti-FASN autoantibody in hepatocellular carcinoma patient using the diagnostic composition for hepatocellular carcinoma.

It is still another object of the present invention to provide a method for screening a therapeutic agent for hepatocellular carcinoma, in which candidate materials expected to treat hepatocellular carcinoma are administered, and the expression levels of anti-FASN autoantibody are assessed before and after administration of the candidate materials, whereby the candidate material reducing the expression level is determined as a therapeutic agent.

Advantageous Effects

When the anti-FASN autoantibody of the present invention is used as a diagnostic marker for hepatocellular carcinoma, hepatocellular carcinoma can be diagnosed with a high specificity and sensitivity using a non-invasive biological sample such as blood, blood plasma, serum, and lymphatic fluid, without performing invasive diagnosis such as tissue biopsy.

Moreover, in the present invention, a sequence reacting with the marker is identified, and therefore hepatocellular carcinoma can be easily diagnosed using the identified amino acid sequence only, without need of designing reactive materials to identify the marker, thereby being effective for the development of a diagnostic kit for hepatocellular carcinoma.

DESCRIPTION OF DRAWINGS

FIG. 3a is the result of selecting ten antibodies, which are highly reactive to HCC cell line, from the B-cell hybridoma clones from K mouse. For selection, the human HCC cell line HepG2 and mouse HCC cell line Hepa-1c1c7 were subjected to intracellular staining, followed by flow cytometric analysis. Thereafter, the highly reactive K1 antibody was first analyzed. FIG. 3B is the result of analyzing the reactivity of the K1 antibody to other cancer cells, in which it was highly reactive to most of the cancer cell lines. FIG. 3c is the result of Western blotting to detect the target antigen of the K1 autoantibody. Total cell lysates of various cancer cell lines were separated on 8-10% SDS-PAGE gel, followed by Western blotting and immunostaining with K1 autoantibody. The target antigen of K1 antibody was detected as a protein of a high molecular weight (>200 KD: indicated by an arrow). FIG. 3d is the result of immunohistochemical staining to examine the intracellular localization of K1 autoantigen. Its expression was localized mainly in the cytoplasm of three liver cell lines (Hepa-1c1c7, Hep3B, Chang), and localized mainly in the membrane of HepG2 cells.

Figure 4:
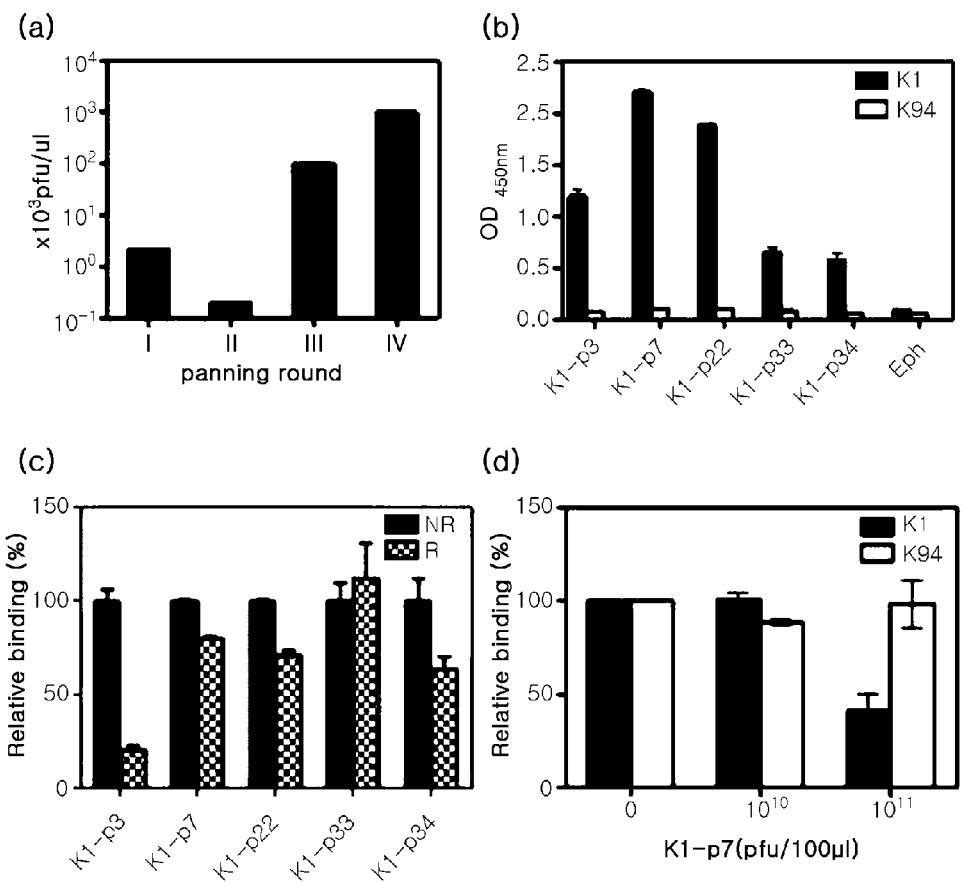

FIG. 4 is the result of panning of the phages against K1 autoantibody to define the epitope sequence of K1 autoantibody using the phage peptide library. After four rounds of panning (FIG. 4a), five phages with different insert peptide sequences were selected (the sequences are represented in FIG. 5), and their reactivity against K1 antibody was analyzed by ELISA. The K1-p7 phage showed the highest reactivity (FIG. 4b). In addition, these epitopes have a cyclic form maintained by two cysteines, and to analyze the conformation-dependency of antibody binding, the cyclic form was reduced and the reactivity was compared (FIG. 4c). To examine whether the phages against K1 autoantibody properly mimic the epitope structure of a K1 antibody-specific antigen that is actually expressed in the cells, competitive inhibition of K1 antibody binding to cells with K1-p7 phage was examined (FIG. 4d). As a result, it was demonstrated that K1-p7 phage showing the highest reactivity to K1 antibody properly inhibits the binding of K1 antibody to cells.

FIG. 5 shows the peptide sequences of the cyclic epitopes, of which the reactivity against K1 antibody was analyzed.

Figure 6:
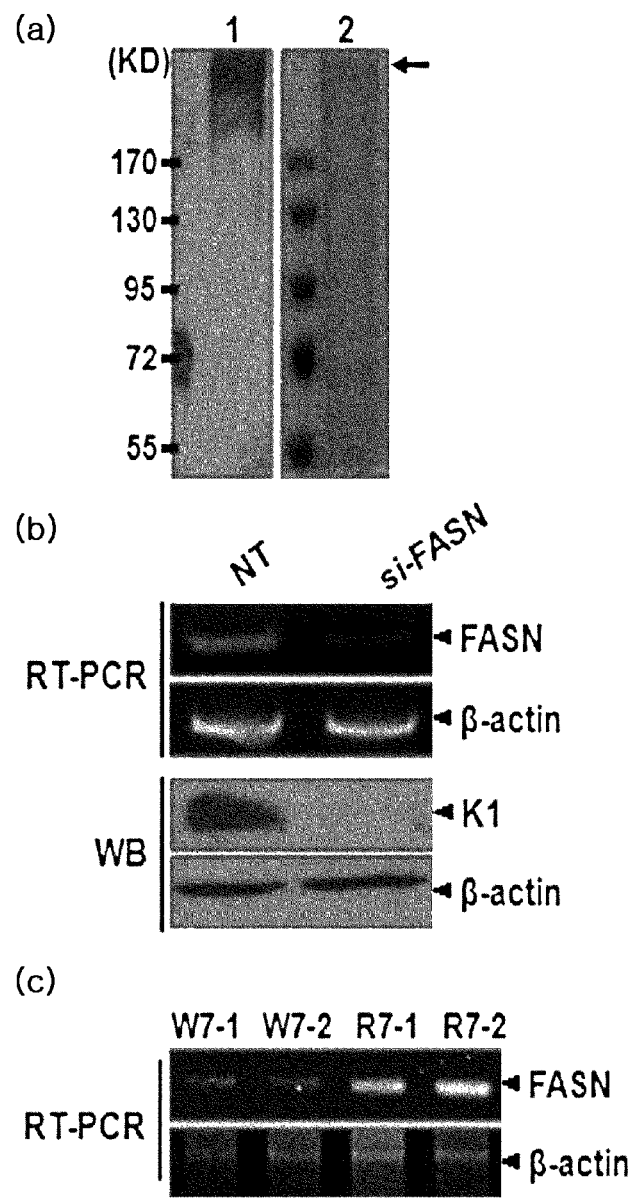

FIG. 6 is the result of identification of K1 autoantigen. FIG. 6a is the result of purifying the antigen protein using K1 antibody in order to identify K1 autoantigen. The purified protein was treated with trypsin, and cleaved to peptides, followed by mass spectrometric analysis for protein identification. As a result, the protein band corresponding to K1 autoantigen was identified as FASN (fatty acid synthase) (the result of sequence analysis is shown in FIG. 7). To re-confirm the result, HepG2 cells were transfected with siRNA against FASN to suppress the expression of FASN, and the reactivity of K1 antibody was analyzed. As shown in FIG. 6b, the protein band stained with K1 autoantibody disappeared when the expression of FASN was shut down. FIG. 6c shows the expression of FASN in the liver tissue of H-ras12V HCC mouse model. FASN expression was remarkably increased in the HCC tissue (R7-1, R7-2), compared to the normal liver tissue of a 7 month-old mouse (W7-1, W7-2).

FIG. 7 is the result of showing that K1 antigen identified by mass spectrometric analysis in FIG. 6a is FASN.

Figure 8:
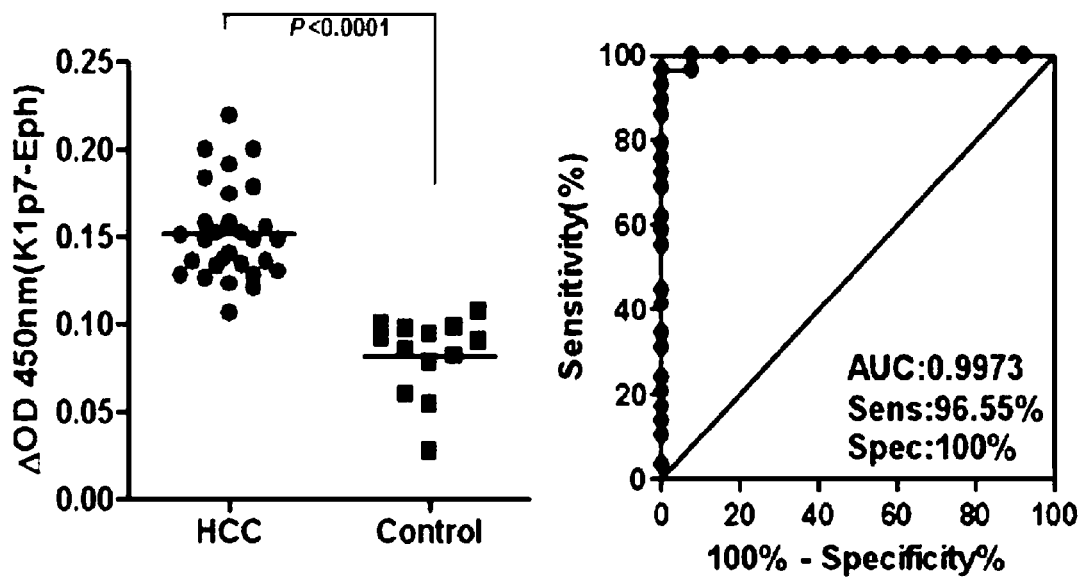

FIG. 8 is the result of detecting autoantibody in the sera from HCC patient and healthy person by ELISA using a mimotope against K1 autoantibody, K1-p7 phage as a coating antigen. As a result, it was found that the sensitivity of this ELISA was 96.55% and specificity was 100% when the cutoff value was 0.114.

Figure 9:
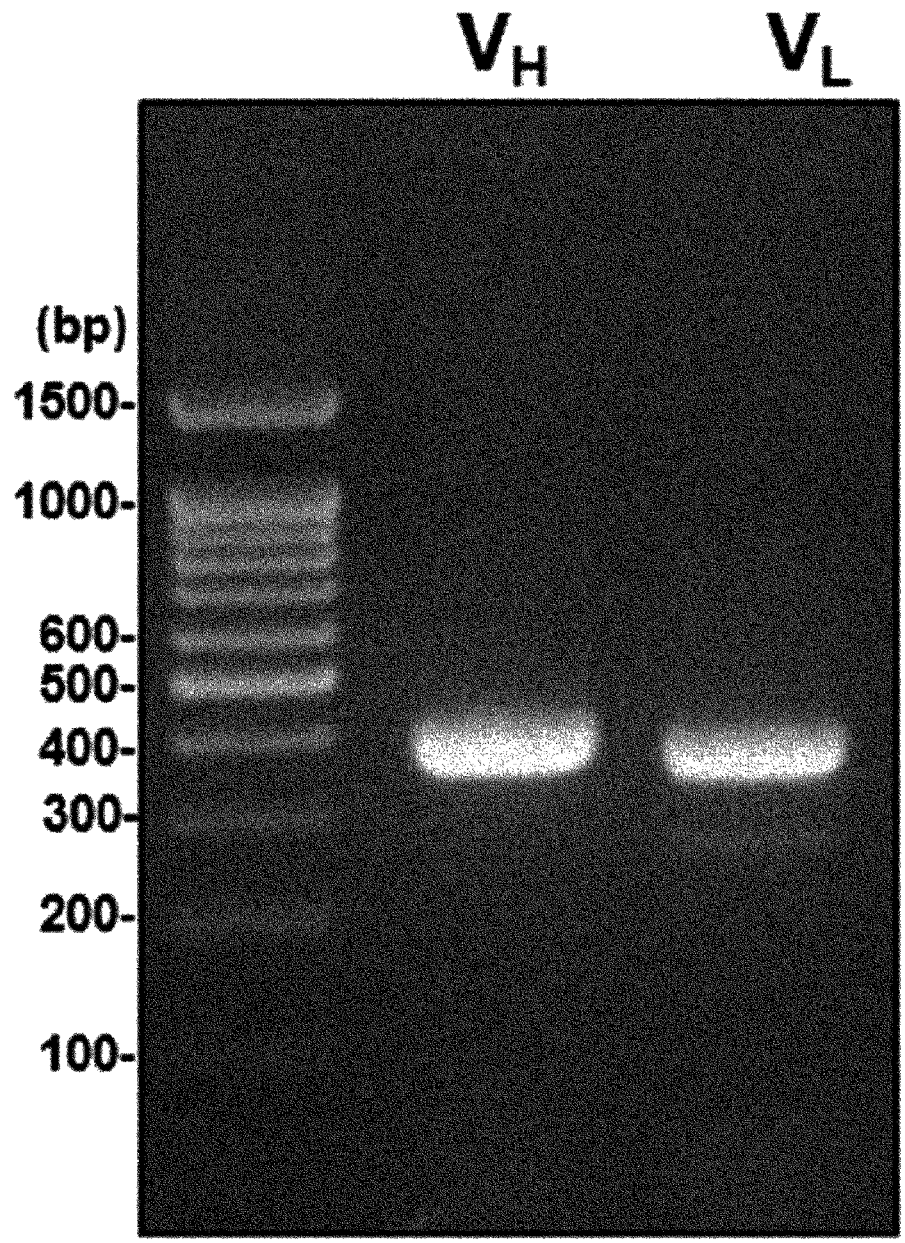

FIG. 9 is the result of 1% agarose gel electrophoresis of variable regions of heavy and light chains ($V_H$, $V_L$) obtained by RT-PCR, in order to determine the base sequence of the antigen biding site of K1 monoclonal antibody. The amplified DNA was cloned into a pCR2.1TOPO vector, and transformed into *E. coli* DH5a, followed by DNA extraction and sequence analysis.

FIG. 10 is the result of sequence analysis of variable region of heavy chain ($V_H$) of K1 antibody. The sequence of 381 bases from the 5'-end were analyzed, and the sequence of amino acid expressed therefrom was marked. CDR (Complementarity Determining Region) was determined from the Kabat sequence database (*Sequences of Proteins of Immunological Interest,* 5th Ed., (1991) U.S. Department of Health and Human Services, National Institutes of Health, Bethesda, Md.).

FIG. 11 is the result of sequence analysis of variable region of light chain ($V_L$) of K1 antibody. The sequence of 363 bases from the 5'-end were analyzed, and the sequence of amino acid expressed therefrom was marked. CDR was determined from the Kabat sequence database.

BEST MODE

Accordingly, in one aspect, the present invention relates to an autoantibody recognizing FASN (fatty acid synthase) or a fragment comprising an antigen-binding site thereof.

As used herein, the term "autoantibody" refers to an antibody formed in response to one of the individual's own body constituents, and is also called "self antibody". In general, individuals do not generate an immune response to their own body constituents, and thus do not produce antibodies against them. In some cases, individuals recognize their own body constituents as antigens to produce antibodies, which causes autoimmune diseases such as systemic lupus erythematosus and rheumatoid arthritis. In other cases, they may produce antibodies against tumor-associated antigens (TAA).

As used herein, the term "anti-FASN autoantibody" means an autoantibody induced against FASN in patients with hepatocellular carcinoma. The present inventors identified autoantibody-expressing B cells from patients with hepatocellular carcinoma, and confirmed expression of a specific autoantibody having a high reactivity with cancer cells, the corresponding antibody is designated as K1 antibody (hereinbelow, referred to as 'anti-FASN antibody', 'K1 antibody' K1 autoantibody' or 'autoantibody K1'). Thereafter, they identified an autoimmune antigen for the corresponding antibody, and demonstrated that the autoantibody is an autoantibody against FASN (anti-FASN autoantibody). Further, the present inventors examined binding sites of the autoantibody in order to identify its specific epitope sequence. As a result, it was confirmed that the autoantibody specifically binds with one or more sequences selected from the group consisting of RMSRRSN (Arg-Met-Ser-Arg-Arg-Ser-Asn; SEQ ID NO. 1), RRRLNRT (Arg-Arg-Arg-Leu-Asn-Arg-Thr; SEQ ID NO. 2), RMRIRRN (Arg-Met-Arg-Ile-Arg-Arg-Asn; SEQ ID NO. 3), HPHPRPR (His-Pro-His-Pro-Arg-Pro-Arg; SEQ ID NO. 4) and MRNRPKR (Met-Arg-Asn-Arg-Pro-Lys-Arg; SEQ ID NO. 5), and more preferably, the autoantibody specifically binds with MRNRPKR (Met-Arg-Asn-Arg-Pro-Lys-Arg; SEQ ID NO. 5).

In general, one antibody molecule has two heavy chains and two light chains, and each heavy and light chain contains an N-terminal variable region. Each variable region consists of three complementarity determining regions (CDR) and four framework regions (FRs), and the complementarity determining region exists as a relatively short peptide sequence, which determines the antigen-binding specificity of an antibody and is maintained by the framework regions of variable region. Preferably, the antibody of the present invention comprises a fragment including an essential sequence which is directly involved in the antigen FASN binding, and more preferably, a fragment directly involved in the binding with a mimotope which mimics the structure of FASN epitope. The autoantibody of the present invention is a part of the variable region of a heavy chain, and may include an autoantibody consisting of the CDR1 sequence of SEQ ID NO. 8, the CDR2 sequence of SEQ ID NO. 9, and the CDR3 sequence of SEQ ID NO. 12, or a fragment including an antigen-binding site thereof. The autoantibody of the present invention may be an autoantibody including all of the sequences of CDR1, CDR2 and CDR3 or a fragment thereof. Further, the autoantibody of the present invention is a part of the variable region of light chain, and may include an autoantibody consisting of the CDR1 sequence of SEQ ID NO. 14, the CDR2 sequence of SEQ ID NO. 16, and the CDR3 sequence of SEQ ID NO. 18, or a fragment including an antigen-binding site thereof. Furthermore, it is apparent that a nucleic acid sequence encoding the sequence is also included in the present invention.

More preferably, the autoantibody of the present invention is a sequence of the variable region of heavy chain, and may be an autoantibody consisting of an amino acid sequence of SEQ ID NO. 20 or a fragment including an antigen-binding site thereof. The autoantibody of the present invention is a sequence of the variable region of light chain, and may be an autoantibody consisting of an amino acid sequence of SEQ ID NO. 22 or a fragment including an antigen-binding site thereof. In addition, the heavy and light chains may be used alone or together depending on the purpose, and any combination of a plurality of CDR sequences and light chains and heavy chains can be made by a conventional genetic engineering method depending on the purpose of those skilled in the art.

The FASN (fatty acid synthase) is an enzyme that functions to produce long-chain saturated fatty acids from acetyl-CoA and malonyl-CoA and is involved in energy metabolism, appetite regulation or the like. Some studies have suggested that fatty acid production of FASN is associated with cancer, and its expression level increases in the tissue of breast cancer and ovarian cancer. However, there is no report on the correlation between hepatocellular carcinoma and FASN. In particular, there is no report on autoantibody production in the development of hepatocellular carcinoma. For the first time, the present inventors revealed that anti-FASN autoantibody is significantly increased in a subject with hepatocellular carcinoma, leading to identification of a peptide sequence of the mimotope of the FASN epitope.

The autoantibody of the present invention may be an intact form consisting of two full-length light chains and two full-length heavy chains as well as a functional fragment of the antibody molecule which is capable of achieving antibody-antigen binding. The functional fragment of the antibody molecule means a fragment having an antigenic binding function, and its length or shape is not limited, exemplified by Fab, F(ab'), F(ab')$_2$ and Fv. However, the functional fragment of the autoantibody of the present invention is not limited to these examples.

The anti-FASN autoantibodies or the fragment comprising an antigen-binding site thereof of the present invention is an antibody that specifically recognizes the amino acid sequence consisting of RMSRRSN (SEQ ID NO. 1), RRRLNRT (SEQ ID NO. 2), RMRIRRN (SEQ ID NO. 3), HPHPRPR (SEQ ID NO. 4) or MRNRPKR (SEQ ID NO. 5), and preferably an antibody that specifically recognizes the amino acid region consisting of the MRNRPKR (SEQ ID NO. 5) sequence.

In another aspect, the present invention relates to a diagnostic composition for hepatocellular carcinoma, comprising an agent capable of assessing the expression level of anti-FASN autoantibody.

As used herein, the term "diagnosis" means confirmation of a pathological state or characteristic. For the purpose of the present invention, the diagnosis is to confirm the development of hepatocellular carcinoma. When the anti-FASN autoantibody of the present invention is used as a diagnostic marker for hepatocellular carcinoma, the development of hepatocellular carcinoma is confirmed by assessing the expression level of the anti-FASN autoantibody of the present invention in the sample of a subject.

As used herein, the term "a diagnostic marker, a marker for diagnosis, or a diagnosis marker" means a material capable of distinguishing hepatocellular carcinoma cells from normal cells, and may include an organic biomolecule such as a polypeptide, a nucleic acid (e.g., mRNA etc.), a lipid, a glycolipid, a glycoprotein, and a sugar (monosaccharide, disaccharide, oligosaccharide etc.), which is expressed at a higher or lower level, as compared to its level in normal cells. For the purpose of the present invention, the diagnostic marker for hepatocellular carcinoma of the present invention is an anti-FASN autoantibody, which is highly expressed in the whole blood, blood, serum, or blood plasma of a subject with hepatocellular carcinoma, as compared to the whole blood, blood, serum, or blood plasma of a subject with normal liver.

As used herein, the term "hepatocellular carcinoma" means a cancer derived from hepatic cells, and encompasses primary hepatocellular carcinoma that begins within the liver and metastatic hepatocellular carcinoma that spread to the liver from other sites. The cause of hepatocellular carcinoma is unclear, but it has been revealed that most of hepatocellular carcinoma patients have liver cirrhosis, and hepatocellular carcinoma frequently occurs in patients with liver cirrhosis or chronic active hepatitis B, or hepatitis B carriers. The present inventors confirmed that the development of hepatocellular carcinoma in a subject can be diagnosed using the autoantibody marker of the present invention with high sensitivity and specificity.

As used herein, the term "agent capable of assessing the expression level of anti-FASN autoantibody" means a molecule used for the detection of markers by assessing the expression level of anti-FASN autoantibodies which is increased in the whole blood, serum and blood plasma, lymphatic fluid, and interstitial fluid of a subject, and preferably an antigen protein that specifically binds to the autoantibody. The analysis method may include Western blotting, ELISA (enzyme linked immunosorbent assay), RIA (radioimmunoassay), radioimmunodiffusion, ouchterlony immunodiffusion, rocket immunoelectrophoresis, immunohistostaining, immunoprecipitation assay, complement fixation assay, FACS and protein chip, but are not limited thereto. By the above analysis methods, the development of hepatocellular carcinoma in patients with hepatocellular carcinoma can be diagnosed by comparing the amount of antigen-antibody complex formed in a subject suspected of having hepatocellular carcinoma to that in the normal control group.

The diagnosis of hepatocellular carcinoma can be achieved by an antibody-antigen reaction between the anti-FASN autoantibody of the present invention and the specific antigen thereof, and the term "antigen-antibody complex", as used herein, refers to binding products of a hepatocellular carcinoma marker, autoantibody to the antigen specific thereto. The amount of formed antigen-antibody complexes may be quantitatively determined by measuring the signal size of a detection label.

Such a detection label may be selected from the group consisting of enzymes, fluorescent substances, ligands, luminescent substances, microparticles, redox molecules and radioactive isotopes, but the present invention is not limited to the examples. Examples of enzymes available as detection labels include, but are not limited to, β-glucuronidase, β-glucosidase, β-galactosidase, urease, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescin, isothiocyanate, rhodamine, phycoerythrin, phycocyanin, allophycocyanin, o-phthaldehyde and fluorescamin. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$. Examples of the radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

As used herein, the term "peptide library" refers to collections of several hundred to several thousand peptides, of which amino acid sequences are artificially changed by combinatorial chemistry. The peptide library technique is used to develop potential drug candidates having biological activity by exploring peptides having amino acid sequences of useful functions using the peptide library, represented by PS-SPCL (Positional-Scanning Synthetic Peptide Combinatorial Library) and OBOPL (One-Bead-One-Peptide Library). However, the type of peptide library available in the present invention is not limited to the examples. Specifically, PS-SPCL is a mixture made of fixing 19 amino acid except cysteine and connecting 19 amino acid mixture to the rest of the region. In the case of hexapeptide, PS-SPCL is a method of exploring 47 million different peptides by screening 114 pools. The other method, OBOPL is a tool of attaching a specific sequence (e.g., pentapeptide) to a resin having polystyrene as a substrate and polyethylene glycol (PEG) as a linker so as to explore the attached sequence. Preferably, a method of identifying the epitope sequence for the autoantibody of the present invention includes the above described identification methods, and any method of identifying epitopes available in the art can be used without limitation. To identify the epitope sequence that binds to the autoantibody of the present invention, the present inventors had employed a cyclic peptide phage display library system which has a cyclic structure formed by 7 amino acids. Preferably, they selected phages that specifically bind with anti-FASN antibody. From the selected phages, only the groups showing a high reactivity with anti-FASN antibody of the present invention were purified, and then treated with a coating antigen. Subsequently, the reactivity with immune antibodies binding to the antigen was confirmed to identify amino acid sequences thereof.

Further, the present inventors investigated anti-FASN antibody as a diagnostic marker for hepatocellular carcinoma by the following demonstration.

First, spleen cells were obtained from a hepatocellular carcinoma mouse model as parent cells, and fused with myeloma cells to produce B cell hybridomas. Among the antibodies secreted from the produced hybridomas, the antibodies showing reactivity with hepatocellular carcinoma cells were selected to isolate autoantibodies available as a marker. Subsequently, the presence of antigens being reactive with the isolated autoantibodies was examined (identification of macromolecular protein of 200 KD or more). In order to more specifically analyze the antigens, the isolated autoantibody K1 was purified in a large amount, and affinity chromatography was performed to identify the antigen protein, and a phage display-peptide library consisting of 7 amino acids was used to identify the epitope sequence binding with the purified autoantibody, thereby confirming the specific epitope sequence. Accordingly, it was demonstrated that the specific antigen protein is FASN, leading to the investigating of a sequence of the structural mimic of the epitope that binds with the autoantibody of the present invention.

In connection to this method, most of the conventional autoantibodies are reported to express in normal cells, except oncofetal proteins, and the number of main epitope is restricted to one, as revealed in the studies on autoantibody against GRP78. Therefore, only the use of a specific epitope is sufficient to detect autoantibody. Various types of autoantibodies were obtained from mouse, and specific antigens recognized thereby were analyzed. Since properties of the antigen proteins are different from each other, it is a practical difficulty to perform an autoantibody-based multiplex detection method by production of each recombinant protein. In particular, it is not easy to prepare intact recombinant proteins of high molecular weight proteins of 200 KD or more. Therefore, for the autoantibody-based multiplex detection method, the present invention was designed in such a way that antigens are presented in a form of expressing each epitope on a common carrier protein.

In addition, to identify the autoantibody, it should be considered that the autoantigen may have a new antigenicity by post translational modification (PTM). In general, autoantigens are expressed in normal cells. However, when the autoantigens associated with tumorigenesis are released from cells after the post translational modification, the neo-antigenic site may have a PTM property upon the production of autoantibodies. In this case, if recombinant proteins of the identified autoantigens are prepared without analysis and reproduction of PTM to perform the detection method, it is impossible to detect the neo-antigenic site having a PTM property.

To solve these problems, the present inventors determined the epitope using a phage peptide library. In view of the fact that the antigenicity of autoantigens is restricted to one or two epitopes of a target protein, they assumed that presentation of single epitopes identified from the peptide library is sufficient for the detection of autoantibody. Consequently, an experiment was performed to identify the autoantibody recognizing the epitope identified from the peptide library. Also, a structure having the highest reactivity with the antibody can be selected by the determination of epitopes with the peptide library, and therefore, a protein sequence of the antigen itself and a modified structure after post-transcriptional modification can be also identified. In addition, since the selected antigen peptide-expressing phages can be readily proliferated, it is very useful for the development of diagnostic methods such as design of proteins chips. On the basis of the above advantages, the present inventors identified the epitopes from the peptide library, leading to identification of the specific epitope sequence which binds with the autoantibody of the present invention. They also confirmed that the identified amino acid fragment can be used in a diagnostic kit for hepatocellular carcinoma.

In still another aspect, the present invention relates to a hybridoma cell line producing an anti-FASN autoantibody.

As used herein, the term "hybridoma cell" means a cell prepared by artificial fusion of two different types of cells. A hybridoma cell line is prepared by fusion of two or more of homogeneous or heterogeneous cells using a material such as polyethylene glycol or a specific species of virus, whereby different functions of the different cells are integrated into one cell. These hybridoma cells can be prepared by fusion of cancer cells proliferated in vitro and any differentiated large cells extracted from the living body. The hybridoma may be represented by lymphocyte hybridomas, including a hybridoma cell generated by fusion of myeloma cell and B cell, a hybridoma cell generated by fusion of T cell and tumor cell thereof, and a hybridoma cell generated by fusion of lymphokine (biologically active material)-producing T cell and tumor cell thereof. It is apparent that the hybridoma cell line of the present invention can be fused and cultured under the optimal conditions for effective production of the autoantibody of the present invention, which are selected by those skilled in the art. In the preferred embodiment of the present invention, B cells were obtained from the spleen of mouse with hepatocellular carcinoma, and fused with the mouse myeloma cell Sp2/0. The fused cells were cultured, and then a B lymphocyte hybridoma producing hepatocellular carcinoma cell-reactive antibody was only selected, which was designated as TAB-K1. The hybridoma was deposited at the Biological Resource Center in the Korea Research Institute of Bioscience and Biotechnology on Jan. 5, 2010 under the Accession No. KCTC 11612BP.

In still another aspect, the present invention relates to a diagnostic kit for hepatocellular carcinoma, comprising an antigen which specifically binds to anti-FASN autoantibody.

The antigen which specifically binds to anti-FASN autoantibody (or polypeptide which specifically binds to the autoantibody) of the present invention encompasses all of the proteins capable of specifically binding to the autoantibody, but is not limited to particular proteins or polypeptides. Preferably, the antigen may include all fragments thereof or variants thereof as long as they can be recognized by the anti-FASN autoantibody. The antigen may consist of at least 7 amino acids, preferably 9 amino acids, and more preferably 12 amino acids or more.

More preferably, the antigen may be an epitope sequence which can be recognized by the autoantibody marker of the present invention. The size or type of the epitope sequence is not limited, as long as it can be recognized by the autoantibody of the present invention. Preferably, the epitope sequence may be a polypeptide sequence consisting of 7 amino acids. The sequence consisting of 7 amino acids may be a sequence including any one or more polypeptides selected from the group consisting of RMSRRSN (Arg-Met-Ser-Arg-Arg-Ser-Asn; SEQ ID NO. 1), RRRLNRT (Arg-Arg-Arg-Leu-Asn-Arg-Thr; SEQ ID NO. 2), RMRIRRN (Arg-Met-Arg-Ile-Arg-Arg-Asn; SEQ ID NO. 3), HPHPRPR (His-Pro-His-Pro-Arg-Pro-Arg; SEQ ID NO. 4) and MRNRPKR (Met-Arg-Asn-Arg-Pro-Lys-Arg; SEQ ID NO. 5), but the type of the sequence to be recognized by the autoantibody of the present invention is not limited to these examples. Using a 7 peptide phage library, the present inventors identified a sequence that specifically recognizes the autoantibody of the present invention. As a result, it was found that the autoantibody of the present invention shows particularly high reactivity to the sequence of MRNRPKR (Met-Arg-Asn-Arg-Pro-Lys-Arg; SEQ ID NO. 5).

In still another aspect, the present invention relates to a method for detecting anti-FASN autoantibody in the sample, taking from a hepatocellular carcinoma patient, using the diagnostic composition for hepatocellular carcinoma.

Preferably, the detection method of anti-FASN autoantibody of the present invention may comprise the steps of (a) assessing the expression level of anti-FASN autoantibody in the sample of a subject suspected of having hepatocellular carcinoma; and (b) comparing the expression level of anti-FASN autoantibody with that of a normal control group.

As used therein, the term "sample" includes, but is not limited to, samples displaying a difference in expression levels of the hepatocellular carcinoma marker anti-FASN autoantibody, such as whole blood, serum, blood, blood plasma, saliva, urine, sputum, lymphatic fluid, cerebrospinal fluid, and interstitial fluid.

Further, the method for assessing the expression level of the autoantibody of the present invention may include Western blotting, ELISA, radioimmunoassay, radioimmunodiffusion, ouchterlony immunodiffusion, rocket immunoelectrophoresis, immunohistostaining, immunoprecipitation assay, complement fixation assay, FACS and protein chip, but is not limited thereto.

The detection method of the anti-FASN autoantibody of the present invention may be performed by comparing the expression level of autoantibody in a subject suspected of having hepatocellular carcinoma with that in a healthy subject. If the subject suspected of having hepatocellular carcinoma displays a higher level of the autoantibody than the normal control group, the corresponding subject can be diagnosed as a patient with hepatocellular carcinoma.

In the detection or diagnosis method of the present invention, any one or more selected from the above methods may be employed, and if necessary, hepatocellular carcinoma can be diagnosed by the two steps of a primary test and a confirmatory test. As such, when two steps are performed to detect the autoantibody of the present invention for the diagnosis of hepatocellular carcinoma, an allogenic sera screening method can be used as the primary test and Western analysis can be used as the confirmatory test to distinguish consistently between positive and false positive reactions.

The detection or diagnosis method of the present invention shows a high consistency of results, even though any of the above methods is adopted to analyze the samples obtained from an identical subject. Therefore, an accurate detection of anti-FASN autoantibody can be achieved, and the development of hepatocellular carcinoma can be diagnosed.

For the detection of the autoantibody of the present invention or diagnosis of hepatocellular carcinoma, the allogenic sera screening method can be performed as follows.

First, the proteins are transferred to a membrane from a microorganism capable of expressing an amino acid sequence recognized by the autoantibody of the present invention. Subsequently, the membrane is blocked, and reacted with a biological sample such as blood, blood plasma, and serum obtained from a subject suspected of having hepatocellular carcinoma, and the binding between antigens immobilized on the membrane and the secondary antibody of the autoantibody of the present invention is confirmed by a typical method, thereby performing a screening.

The 'microorganism capable of expressing an amino acid sequence' used in the above step may be a bacteria transformed with an expression vector having a gene encoding the antigen for anti-FASN autoantibody or a bacteria transformed with a general expression vector, and preferably, the antigen includes FASN or a fragment thereof that can be recognized by the autoantibody of the present invention. More preferably, the antigen is an epitope for the autoantibody of the present invention, and may be RMSRRSN (SEQ ID NO. 1), RRRLNRT (SEQ ID NO. 2), RMRIRRN (SEQ ID NO. 3), HPHPRPR (SEQ ID NO. 4) or MRNRPKR (SEQ ID NO. 5) identified by the present inventors, and most preferably, MRNRPKR (Met-Arg-Asn-Arg-Pro-Lys-Arg; SEQ ID NO. 5).

In the above method, the membrane, to which proteins are transferred, may be any membrane having the capability of attaching proteins, such as NC (nitrocellulose), nylon, and PVDF, and the type of the membrane is not limited to these examples.

In the above method, a variety of proteins can be transferred to the membrane as follows. In the case of a phage-expressing microorganism, the proteins can be transferred to the membrane by contacting the membrane on the medium and separating therefrom after plaque formation. In the case of a microorganism transformed with a general expression vector, the membrane is contacted on the medium and separated therefrom, and then frozen and thawed to rupture the cell wall, thereby exposing the proteins on the membrane.

Further, when the blood of a subject is reacted with the membrane, it is preferable that the dilution ratio is controlled depending on properties of the blood (viscosity), and also properly determined by those skilled in the art. Preferably, the blood may be diluted at a ratio of 1:200.

Thereafter, the reaction may be examined by a colorimetric method using an enzyme or a fluorescent substance, a radiometric assay, and immunohistochemistry without limitation, and preferably a rapid and simple colorimetric method using an enzyme.

In the colorimetric method using an enzyme, an antigen-antibody complex is bound with a secondary antibody that is labeled with an enzyme catalyzing a colorimetric reaction of a substrate, and then a colorimetric substrate is added, followed by confirmation of the color development. As the enzyme available in the diagnostic method of the present invention, any enzyme used in the conventional enzyme-colorimetric method can be adopted without limitation, such as alkaline phosphatase, peroxidase, and glucose oxidase.

Meanwhile, Western blot may be adopted to detect the autoantibody of the present invention or to diagnose hepatocellular carcinoma. In this method, a gene encoding the amino acids recognized by anti-FASN autoantibody of the present invention is cloned to an expression vector that is prepared to produce fusion proteins, and then E. coli was transformed with the recombinant plasmid. The proteins extracted from E. coli is subjected to SDS-PAGE (sodium dodecyl sulfate-polyacrylamide gel electrophoresis), and then the proteins are transferred to a proper membrane. Thereafter, as in the allogenic sera screening method, the membrane is reacted with the blood of a subject suspected of having hepatocellular carcinoma, so as to detect the antibody.

In the method, the expression vector to be used in the cloning of the gene encoding the antigen for the autoantibody of the present invention may include a gene of GST (glutathione-S-transferase) or β-galactosidase, and preferably a vector that can be stably expressed in E. coli.

Moreover, ELISA may be adopted to detect the autoantibody of the present invention or to diagnose hepatocellular carcinoma, in which an ELISA plate is coated with the identified antigen sequence, and treated with a primary antibody, washed, and then treated with a secondary antibody, so as to detect the reaction between the antigen and the primary antibody. In the preferred embodiment of the present invention, the epitope sequence reacting with the autoantibody of the present invention was identified using a 7 peptide phage library, and the identified sequence was used to react with a primary antibody, followed by reaction with IgGAM-HRP. Then, the formation of antigen-antibody complex and the amount thereof were examined. As a result, a distinct pattern was observed between the sera of the healthy subject and the hepatocellular carcinoma subject.

When anti-FASN autoantibody is detected or hepatocellular carcinoma is diagnosed by the above method, hepatocellular carcinoma can be diagnosed with a high specificity and sensitivity. In the preferred embodiment of the present invention, it was found that hepatocellular carcinoma patients can be diagnosed and distinguished from healthy subjects to the level of about 97% sensitivity and 100% sensitivity by ELISA (Enzyme-linked immunosorbent assay).

In still another embodiment, the present invention relates to a method for screening a therapeutic agent for hepatocellular carcinoma, in which materials expected to treat hepatocellular carcinoma are administered, and the expression levels of anti-FASN autoantibody are assessed before and after administration of the candidate materials, whereby the candidate material reducing the expression level is determined as a therapeutic agent.

More particularly, the method for screening a therapeutic agent for hepatocellular carcinoma of the present invention may include the steps of (a) assessing the expression level of anti-FASN autoantibody; (b) administering candidate materials expected to treat hepatocellular carcinoma; and (c) confirming a reduction in the expression level of anti-FASN autoantibody, compared to step (a).

The step of assessing the expression level of anti-FASN autoantibody may be performed by the above-described method of assessing the expression level that is typically employed in the art, without limitation, and exemplified by Western blotting, ELISA, radioimmunoassay, radioimmunodiffusion, ouchterlony immunodiffusion, rocket immunoelectrophoresis, immunohistostaining, immunoprecipitation assay, complement fixation assay, FACS, and protein chip.

The materials expected to treat hepatocellular carcinoma are also called candidate materials, and the materials are not particularly limited, as long as they are expected to directly or indirectly ameliorate or improve hepatocellular carcinoma. The material includes all materials expected to show therapeutic effects, such as compounds, genes, and proteins. In the screening method of the present invention, the expression levels of anti-FASN autoantibody are assessed before and after administration of the candidate materials, and the candidate material showing a reduction in the expression level can be determined as a therapeutic agent for hepatocellular carcinoma.

MODE FOR INVENTION

Example 1

Figure 1:
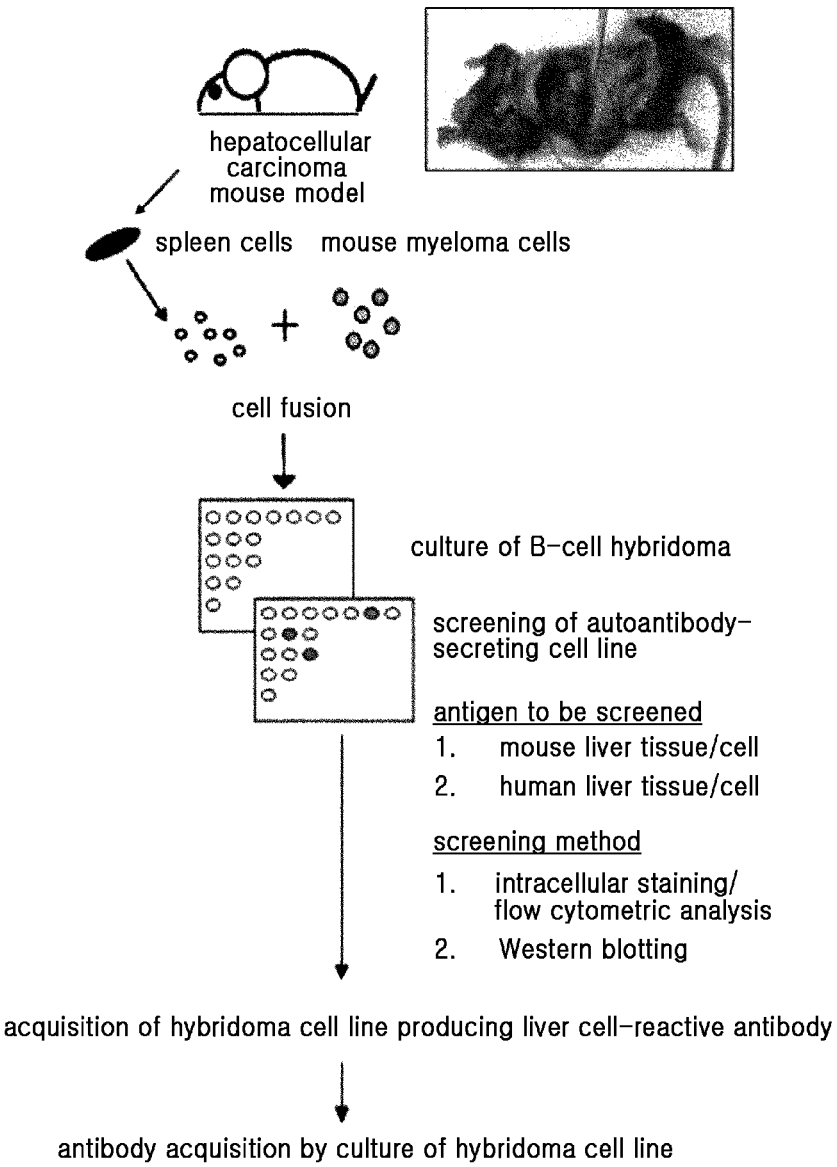
FIG. 1 is an overview of the method of obtaining hepatocellular carcinoma-associated autoantibody from hepatocellular carcinoma mouse model. H-ras12V transgenic HCC mouse model (characterized by the occurrence of hepatocellular carcinoma at 8-10 months of age) was acquired, and splenocytes from H-ras12V transgenic mice at 10 months or older were fused with the mouse myeloma cells Sp2/0, and selection of B-cell hybridomas producing HCC-associated autoantibodies was performed.

Acquisition of Disease Mouse Model and Autoantibody-Producing Cells Using the Same FIG. 1 is an overview of the method of obtaining hepatocellular carcinoma-associated autoantibody from hepatocellular carcinoma mouse model. H-ras12V transgenic HCC mouse model, characterized by the occurrence of hepatocellular carcinoma at 8-10 months of age, was acquired, and splenocytes from the mouse models that developed hepatocellular carcinoma were fused with the mouse myeloma cells Sp2/0. The fused cells were primarily selected using HAT medium, and cells forming clones were separately cultured. B-cell hybridomas producing HCC-associated autoantibodies were only selected from the cell media, and maintained. The reactivity of the B-cell hybridoma medium to HCC cells was examined by the following method in Example 2.

Example 2

Figure 2:
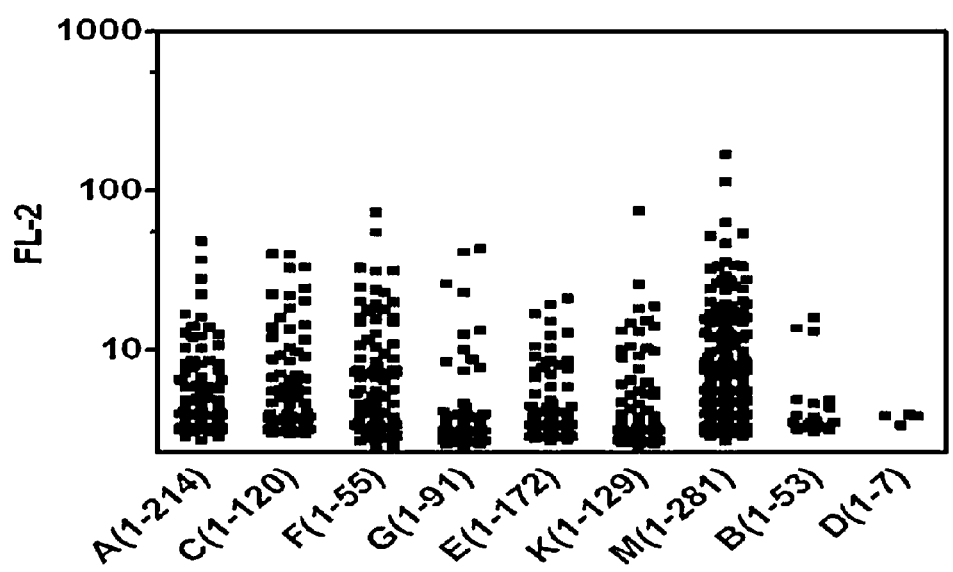
FIG. 2 is the result of analyzing the reactivity of autoantibodies against hepatocellular carcinoma cells, in which the autoantibodies are produced by B cell hybridoma clones derived from H-ras12V transgenic HCC mouse model. The hepatocellular carcinoma cell line HepG2 was fixed with paraformaldehyde and permeabilized with a permeabilization reagent, and then treated with autoantibodies. After treatment with a primary antibody, the residual antibodies were washed out, and the cells were treated with a fluorescent-labeled secondary antibody, followed by flow cytometric analysis. Many B-cell hybridoma clones being highly reactive to HepG2 cells were observed in F or M mouse showing a high development of hepatocellular carcinoma, whereas fewer B-cell hybridoma clones and lower reactivity of autoantibodies produced therefrom were observed in B or D mouse which did not develop hepatocellular carcinoma despite being transgenic.
Figure 3:
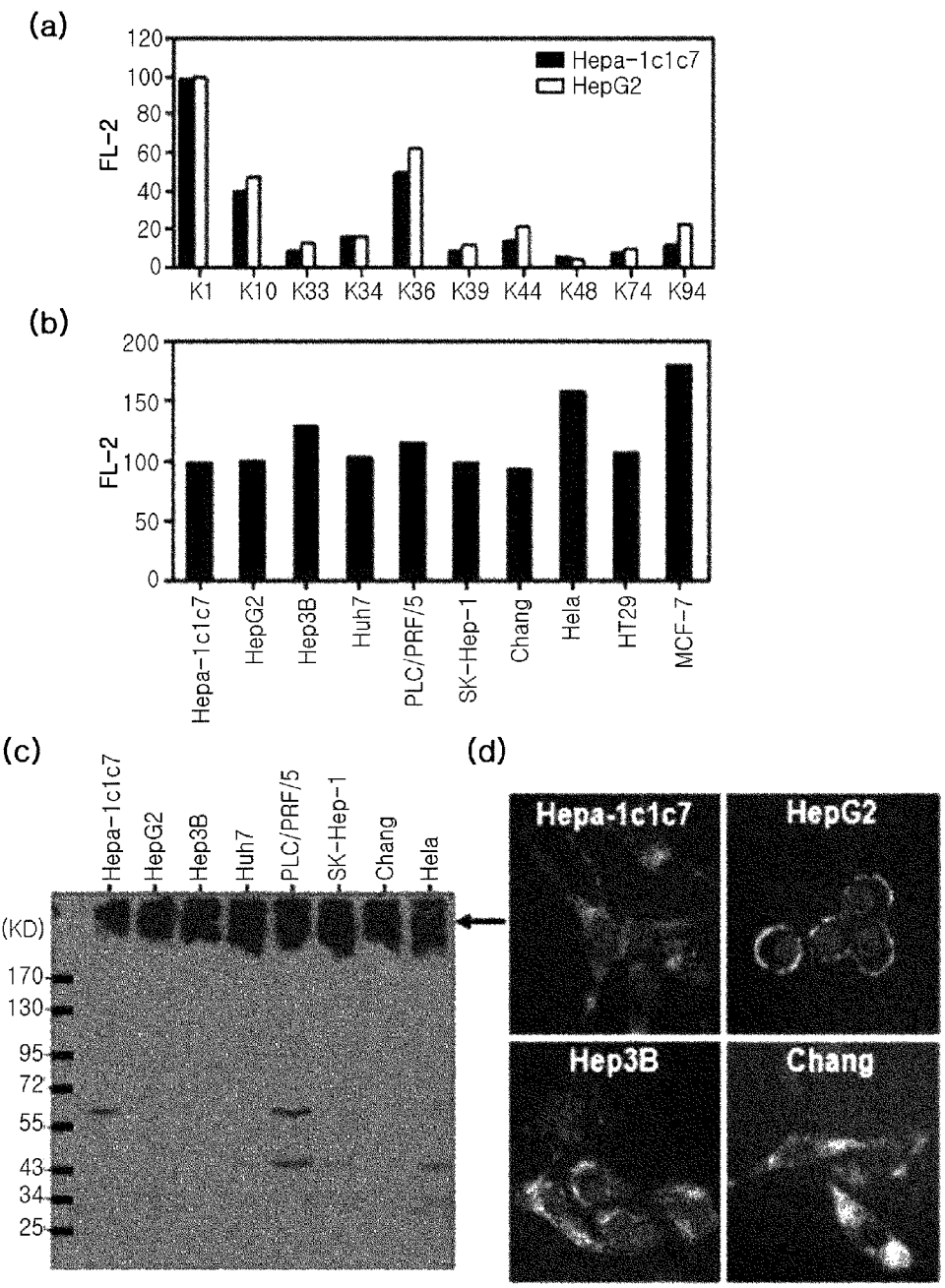
FIG. 3 is the result of analyzing a monoclonal antibody K1, which is produced from a K1 clone that is an autoantibody-producing B cell derived from K mouse among H-ras12V HCC mouse models.

Flow Cytometric Analysis for Detection of Autoantibody Generated by B-Cell Monoclone To select antibodies reactive to hepatocellular carcinoma cells from the antibodies that were produced by the B-cell hybridomas obtained from cancer mouse model, intracellular staining of fixed and permeabilized cancer cell lines was performed, followed by flow cytometric analysis. 70-80% confluent HepG2 or Hepa-1c1c7 cells were treated with trypsin, and detached from a cell culture plate, and washed with PBS. Then, the cells were treated with a Cytofix/Cytoperm solution (BD) (1000 μl per $2 \times 10^5$ cells) at 4° C. for 20 min for fixation and permeabilization. After the incubation, 1 ml of Cytowash/Cytoperm solution (BD) was added, and vortexed, and then centrifuged at 1700 rpm for 5 min to obtain cell pellets. After washing the cells, 50 µl of primary antibody solution (B-cell hybridoma culture media or purified primary antibody solution) was added thereto, followed by incubation at 4° C. for 40 min. Thereafter, the cells were washed several times, and treated with anti-mouse Igs-RPE (DaKo) as a secondary antibody at 4° C. for 40 min. Then, the cells were washed three times, and cell pellet was suspended with 300 µl of PBS, followed by analysis using FACScalibur (BD). The mean fluorescence intensities corresponding to antibody reaction were measured, and compared with each other. Instead of the primary antibody, 50 µl of complete DMEM medium was added to a control group showing no antibody reaction. FIG. 2 and FIGS. 3a and 3b are the results of detecting autoantibody by intracellular staining as described above.

Example 3

Western Blotting Analysis for K1-Autoantigen

As a sample for protein analysis, the subject cells were collected and lysed in RIPA buffer (PBS containing 0.1% SDS, 0.1% sodium deoxycholate, 1.0% NP40, protease inhibitor cocktail (Roche)), or lysed in SDS-PAGE sample buffer and heated. Bradford assay was performed for protein quantification. The prepared protein sample was run on 8%~10% reduced SDS-PAGE, and transferred onto a PVDF membrane. Thereafter, the membrane was blocked with 5% skim milk (TBS), and treated with a primary antibody. The purified K1 antibody was used at a concentration of 10 µg/ml as a primary antibody. After treatment of primary antibody, the membrane was washed with TBST (0.02% Tween-20 containing TBS), and treated with secondary antibody (anti-mouse IgGAM-HRP). Then, the protein band corresponding to antibody reaction was confirmed by ECL. β-actin was used as a protein loading control for result comparison. As shown in FIG. 3c, it was found that the K1 antigen is a protein of a high molecular weight (>200 KD) and overexpressed in most cancer cells lines.

Example 4

Purification of K1 Monoclonal Antibody

For analysis of K1 autoantibody-specific antigen, purified monoclonal autoantibodies are needed. Therefore, in the present invention, a cell culture medium where K1 autoantibody-producing clones were mass-produced, or a K1 autoantibody-producing cell, was peritoneally injected into mice. The ascites fluid was obtained, and used for the purification of K1 autoantibody. The isotype of K1 autoantibody was found to be IgM. For the purification of IgM, a MBP (Mannose-binding protein)-immobilized agarose (Pierce) or Protein L agarose was used. The purified antibody was confirmed by SDS-PAGE and Coomassie staining, followed by Bradford assay for protein quantification.

Example 5

Intracellular Localization of K1-Autoantigen Visualized by Intracellular Fluorescent Staining To examine the intracellular localization of the K1 antibody-specific antigen protein, cells were cultured on a coverslip, and then washed with PBS, followed by staining in the same manner as in the intracellular staining method. Confocal laser microscopy (Zeiss) was performed. In this connection, the purified K1 antibody was used as a primary antibody at a concentration of 5 µg/ml, and anti-mouse IgGAM-FITC (Sigma) was used as a secondary antibody. The stained coverslip was treated with a mounting solution containing DAPI, and placed on a slide. As shown in FIG. 3d, expression of the K1 antibody-specific antigen was localized mainly in the cytoplasm of Hepa-1c1c7, Hep3B, and Chang cells, with the exception of HepG2 cell, in which the expression was incorporated in the plasma membrane.

Example 6

Biopanning of Mimotope Phage Against K1 Autoantibody

During the biopanning of mimotope phage against K1 autoantibody, 7 amino acids were expressed as random sequences, and a phage display cyclic peptide library system (Ph.D.-C7C Phage Display Peptide Library kit; New England Biolabs Inc.), which is a cyclic random hepta-peptide phage library formed by cysteine residues at both ends, was used, performed in accordance with manufacturer's instructions. Briefly, $2\times10^{11}$ phage virions were incubated with 300 ng of K1 antibody in 200 µl of TBST solution at room temperature for 20 min, and reacted with 25 µl of protein L-agarose beads that were treated with a blocking solution (0.1 M $NaHCO_3$ (pH 8.6), 5 mg/ml BSA, 0.02% $NaN_3$) at room temperature for 15 min. An antibody-virion-protein L-agarose complex was formed, and washed with TBST, followed by elution of the virions bound to antibody in 1 ml of buffer (0.2 M Glycine-HCl (pH 2.2), 1 mg/ml BSA). Immediately, the eluate was neutralized with 1 M Tris-HCl (pH 9.1). A part of the eluted phages was used for phage titration, and the rest was used for phage amplification. Panning of the amplified phages was performed in the above method, and after four rounds of biopanning of the phage library, five phages with different epitope sequences were obtained. As the biopanning using K1 antibody was repeated, the number of amplified phage was increased to 10 times (FIG. 4a) and therefore, the specific phages were well amplified. The epitope sequences of the obtained phages are shown in FIG. 5.

Example 7

ELISA for Detection of Antibody-Specific Epitope Expressing Phage

To examine the reactivity of selected phages against K1 autoantibody, the phage was used as a coating antigen, and K1 antibody was used as a primary antibody to perform ELISA. The 96-well Maxisorp plate was coated with purified phage ($10^{10}$ pfu/well) in 100 ul of a coating buffer (0.1 M sodium carbonate buffer (pH 8.6)). For antigen coating, the phage-coated plate was stored at 4° C. for 16 hrs or longer. After phage coating, 300 µl of 5% skim milk solution was added, and incubated at room temperature for 1 hr for blocking the plate. After completing the blocking, the plate was washed with TBST (TBS containing 0.2% Tween-20) five times, and 100 ng/100 µl of K1 antibody was added thereto, followed by incubation at room temperature for 1 hr and 30 min. After incubation, the plate was washed with TBST five times, and treated with a secondary antibody, anti-mouse IgGAM-HRP (Sigma) diluted at a ratio of 1:2000, followed by incubation at room temperature for 1 hr and 30 min. Then, the plate was washed with TBST five times, and TMB solution (Pierce) was used as a substrate of HRP for color development, and absorbance was measured at 450 nm to quantify antigen-antibody reaction. Five phages obtained from the biopanning with K1 autoantibody (FIG. 5) were used as coated phages, and among them, K1-p7 showed the highest reactivity (FIG. 4b). The phage peptide display library utilized in the present invention is characterized by a cyclic hepta-peptide phage library. In this case, a conformation-dependent epitope is generally obtained. To examine whether the phages against K1 antibody of the present invention have a conformational characteristic or express an amino acid sequence-dependent epitope, the cyclic structure of the phage epitope was converted into a linear form by treatment of DTT, and then the reactivity of treated phages against the antibody was examined (FIG. 4c). For reduction of the cyclic structure, $10^{10}$ phages were diluted in 20 µl of TBS, and reacted with 0.25 µl of 1 M DTT at 55° C. for 20 min, and then reacted with 0.25 µl of 2.5 M iodoacetamide at room temperature for 20 min. Thereafter, the reduced phages were diluted with a coating buffer, and their reactivity was measured by ELISA (FIG. 4c). As a result, all five phages maintained at 50-80% reactivity compared to those before reduction, which means that the reactivity of five phages to K1 antibody is dependent on the characteristics of peptide sequences rather than the conformation of antigen.

Example 8

Competitive Inhibition of Antibody Reaction to Confirm Whether the Phage Mimics the Epitope Structure of a Specific Autoantigen To examine whether the selected phages properly mimic the epitope, competitive inhibition of antibody reaction with the phages were confirmed by flow cytometric analysis of the reaction of K1 antibody with intracellular antigen protein. The flow cytometric analysis was performed as described in Example 2. As a primary antibody, K1 antibody was only used or the mixture of K1 antibody and K1-p7 phage pre-reacted for 1 hr was used, compared to each other. At this time, 100 ng of K1 antibody and $10^{11}$ K1-p7 phages were used. Five K1 antibody-reactive phages were obtained, but K1-p7, being highly reactive to K1 antibody, was only used in the test of competitive inhibition and further experiment. As shown in FIG. 4d, K1-p7 phage was found to competitively inhibit 50% or more of the binding of K1 antibody to HepG2 cells under the above described conditions, which demonstrates that K1p7 phage properly mimics the epitope structure of K1 antibody-specific target antigen.

Example 9

Purification of Antigen Protein for Autoantigen Identification and Protein Identification by Mass Spectrometric Analysis To identify the K1 antibody-specific antigen protein, K1 antibody was conjugated to a resin, and used for immunoprecipitation of K1 antibody-binding protein in the HepG2 cell lysate. For conjugation of K1 antibody to the resin, an aminolink resin (Pierce) and sodium cyanoborohydride were used. After preparation of the K1 antibody-conjugated resin, the resin was reacted with Hepa-1c1p cell lysate, and washed with PBS. Specific elution of antigen proteins by competitive inhibitor was performed using $10^{12}$ K1-p7 phages dissolved in 100 µl of PBS. The eluted antigen protein solution was concentrated using speedvac, and separated on an 8-10% SDS-PAGE. A part of them was used to confirm the presence of K1 antigen by Western blotting, and the rest was subjected to Coomassie staining, followed by analysis of protein bands. The bands corresponding to those probed by K1 antibody were excised and used for protein identification by mass analysis (FIG. 6a). As a result, the K1 antibody-reactive antigen was found to be FASN (fatty acid synthase) (FIG. 7).

Example 10

Knockdown of FASN Using siRNA and Reduction of K1 Antibody Reaction Thereby

For further analysis of the protein that was identified by mass analysis, K1 antibody reaction against HepG2 cells, which were treated with FASN expression-inhibiting siRNA, was examined. FASN expression-inhibiting siRNA provided by Bioneer was used, and RT-PCR for analysis of FASN expression was performed using a primer set consisting of 5'-CCCCTGATGAAGAAGGATCA-3' (SEQ ID NO. 6) as a forward primer and 5'-ACTCCACAGGTGGGAACAAG-3' (SEQ ID NO. 7) as a reverse primer. Cell lysate, where FASN expression was inhibited by siRNA, was analyzed by Western blotting of K1 antibody (FIG. 6b). As a result, it was found that the reaction against K1 antibody was greatly reduced, which re-confirms that K1 antibody-specific antigen protein is FASN.

Example 11

RT-PCR for FASN Expression Analysis in Liver Tissue of HCC Mouse

The liver tissues (R7-1, R7-2, W7-1, W7-2) were obtained from two mice of seven month-old H-ras12V and normal mice each, and total RNA was extracted therefrom using a RNA purification column (Qiagene). 1 µg of the total RNA was reacted with reverse transcriptase (Gibco) to synthesize cDNA, and FASN expression was analyzed using the primer set used in Example 10. As shown in FIG. 6c, FASN expression in the liver tissue from H-ras12V mice developing hepatocellular carcinoma was increased about 2-fold more than in the normal tissues.

Example 12

ELISA for Diagnosis of Hepatocellular Carcinoma by Use of K1-Specific Phage, K1-p7

Titration of K1-p7 phages purified by PEG precipitation was performed to determine the phage concentration, and each well of a 96-well ELISA plate was treated with $1\times10^{10}$ pfu of phages diluted in 100 µl of 0.1 M ammonium carbonate buffer (pH 9.6), followed by incubation at 4° C. for more than 16 hrs. Thereafter, the residual antigens were removed, and 300 µl of protein-free blocking buffer (Pierce) was added to each well for blocking Subsequently, each well was washed five times with TBS containing 0.1% Tween-20, and treated with the sera from hepatocellular carcinoma patient and normal subject as a primary antibody. The human serum is a mixture of various proteins and antibodies, and induces non-specific reaction. Therefore, in the present invention, 20 µg of the cell lysate protein of ER2780 which is a host cell used for phage amplification and $10^{11}$ M13 bacteriophages (empty phage; Eph) without a peptide library sequence was reacted with 0.1 µl of each serum sample for 90 min for pre-immunoadsorption, and diluted with a protein-free blocking buffer to prepare 100 µl of solution, and used as a primary antibody for phage ELISA. The primary antibody reaction was performed at room temperature for 1 hr, and the unreacted antibodies were washed with a washing solution five times. Anti-human IgGAM-HRP (Abcam) was diluted in the protein-free blocking buffer at a ratio of 1:2000, and 100 µl thereof was used as a secondary antibody, followed by incubation at room temperature for 1 hr. Thereafter, washing was performed five times, and 100 µl of TMB solution was added for HRP reaction. Then, absorbance was measured at 450 nm. As shown in FIG. 8, the serum of a patient with hepatocellular carcinoma was clearly distinguished from that of normal subjects, and 96.55% sensitivity and 100% specificity were observed by ROC curve. These results indicate that ELISA composed of a mimotope against anti-FASN autoantibody, K1-p7 phage can be used as an efficient diagnostic method of hepatocellular carcinoma.

Example 13

Sequence Analysis of Antigen-Specific Variable Region of K1 Antibody

Total RNA was extracted from TAB-K1 (Accession No. KCTC 11612BP), which is a K1 monoclonal antibody-producing B cell hybridoma. $5 \times 10^6$ cells were cultured and recovered, followed by purification using an RNA purification kit (QIAgen). 5 µg of the purified RNA was subjected to reverse transcription using a Superscript III reverse transcriptase. With respect to the resulting cDNA, variable region-specific primers and Tag DNA polymerase (Bioneer) were used to amplify the regions corresponding to the heavy ($V_H$) and light chains ($V_L$) of the antibody. The sequences of the variable region-specific primers were the same as the sequences used by Wang et al., (J. Immunol. Methods 233 (2000) 167-177). Since K1 antibody is IgM, primers suitable for the amplification of variable regions of IgM were selected, and the sequences thereof are as follows (codes of R, Y, M, etc in the sequence are mixed base codes of basic base sequences, as follows; R=a,g Y=c,t M=a,c K=g,t S=c,g W=a,t V=a,c,g N=a,c,g,t).

1. Mouse heavy chain FR1 region high degeneracy primer
(SEQ ID NO. 24)
5'- ctt ccg gaa ttc SAR GTN MAG CTG SAG SAG TCW GG -3'

2. Mouse IgM heavy chain constant region primer
(SEQ ID NO. 25)
5'- gga aga tct GAC ATT TGG GAA GGA CTG ACT CTC-3'

3. Mouse kappa chain constant region primer
(SEQ ID NO. 26)
5'- GGT GCA TGC GGA TAC AGT TGG TGC AGC ATC-3'

4. Mouse kappa chain FR1 region universal degenerate primer
(SEQ ID NO. 27)
5'-gg gag ctc GAY ATT GTG MTS ACM CAR WCT MCA-3'

The amplified DNA was examined by agarose gel electrophoresis, and then cloned into a pCR2.1TOPO vector (Invitrogen), followed by transformation into *E. coli* DH5a. The vector DNA was extracted from the transformed cells, and the corresponding sequence was analyzed.

---

The invention claimed is:

1. An isolated monoclonal antibody recognizing FASN (fatty acid synthase) or a fragment comprising an antigen-binding site thereof, wherein the monoclonal antibody or antigen binding fragment thereof recognizes the amino acid sequence of MRNRPKR (SEQ ID NO: 5).

2. The isolated monoclonal antibody or antigen binding fragment thereof according to claim 1, wherein the monoclonal antibody comprises CDR1 sequence of SEQ ID NO: 8, CDR2 sequence of SEQ ID NO:10, and CDR3 sequence of SEQ ID NO: 12 as a CDR (Complementarity determining region) sequence of heavy chain variable region; and CDR1 sequence of SEQ ID NO: 14, CDR2 sequence of SEQ ID NO: 16, and CDR3 sequence of SEQ ID NO: 18 as a CDR (Complementarity determining region) sequence of light chain variable region.

3. The isolated monoclonal antibody or antigen binding fragment thereof according to claim 1, wherein the monoclonal antibody comprises amino acid sequence of SEQ ID NO: 20 as a heavy chain variable region and amino acid sequence of SEQ ID NO: 22 as a light chain variable region.

4. An isolated hybridoma cell line identified by the Accession No. KCTC 11612BP, and wherein the hybridoma cell line produces a monoclonal antibody that recognizes the amino acid sequence of MRNRPKR (SEQ ID NO: 5).

5. A diagnostic composition for hepatocellular carcinoma, comprising the monoclonal antibody of claim 1.

6. A diagnostic kit for detecting hepatocellular carcinoma, comprising the composition of claim 5.

7. A method of detecting FASN, comprising:
 a) contacting a sample with the antibody of claim 1; and
 b) detecting binding of the antibody of claim 1 to FASN.

* * * * *

SEQUENCE LISTING

```
<160> NUMBER OF SEQ ID NOS: 36

<210> SEQ ID NO 1
<211> LENGTH: 7
<212> TYPE: PRT
<213> ORGANISM: Artificial Sequence
<220> FEATURE:
<223> OTHER INFORMATION: 7 peptide antigen for FASN

<400> SEQUENCE: 1

Arg Met Ser Arg Arg Ser Asn
1               5

<210> SEQ ID NO 2
<211> LENGTH: 7
<212> TYPE: PRT
<213> ORGANISM: Artificial Sequence
<220> FEATURE:
<223> OTHER INFORMATION: 7 peptide antigen for FASN

<400> SEQUENCE: 2

Arg Arg Arg Leu Asn Arg Thr
1               5

<210> SEQ ID NO 3
<211> LENGTH: 7
<212> TYPE: PRT
<213> ORGANISM: Artificial Sequence
<220> FEATURE:
```

-continued

<223> OTHER INFORMATION: 7 peptide antigen for FASN

<400> SEQUENCE: 3

Arg Met Arg Ile Arg Arg Asn
1               5

<210> SEQ ID NO 4
<211> LENGTH: 7
<212> TYPE: PRT
<213> ORGANISM: Artificial Sequence
<220> FEATURE:
<223> OTHER INFORMATION: 7 peptide antigen for FASN

<400> SEQUENCE: 4

His Pro His Pro Arg Pro Arg
1               5

<210> SEQ ID NO 5
<211> LENGTH: 7
<212> TYPE: PRT
<213> ORGANISM: Artificial Sequence
<220> FEATURE:
<223> OTHER INFORMATION: 7 peptide antigen for FASN

<400> SEQUENCE: 5

Met Arg Asn Arg Pro Lys Arg
1               5

<210> SEQ ID NO 6
<211> LENGTH: 20
<212> TYPE: DNA
<213> ORGANISM: Artificial Sequence
<220> FEATURE:
<223> OTHER INFORMATION: Forward primer for FASN

<400> SEQUENCE: 6
cccctgatga agaaggatca                                              20

<210> SEQ ID NO 7
<211> LENGTH: 20
<212> TYPE: DNA
<213> ORGANISM: Artificial Sequence
<220> FEATURE:
<223> OTHER INFORMATION: Reverse primer for FASN

<400> SEQUENCE: 7
actccacagg tgggaacaag                                              20

<210> SEQ ID NO 8
<211> LENGTH: 5
<212> TYPE: PRT
<213> ORGANISM: Artificial Sequence
<220> FEATURE:
<223> OTHER INFORMATION: K1 Heavy chain variable region CDR1

<400> SEQUENCE: 8

Ser Tyr Gly Ile Ser
1               5

<210> SEQ ID NO 9
<211> LENGTH: 15
<212> TYPE: DNA
<213> ORGANISM: Artificial Sequence
<220> FEATURE:
<223> OTHER INFORMATION: K1 Heavy chain variable region CDR1

<400> SEQUENCE: 9

```
agctatggta taagc                                                      15
```

\<210\> SEQ ID NO 10
\<211\> LENGTH: 17
\<212\> TYPE: PRT
\<213\> ORGANISM: Artificial Sequence
\<220\> FEATURE:
\<223\> OTHER INFORMATION: K1 Heavy chain variable region CDR2

\<400\> SEQUENCE: 10

```
Glu Ile Tyr Pro Arg Ser Gly Asn Thr Tyr Tyr Asn Glu Lys Phe Lys
1               5                   10                  15
Gly
```

\<210\> SEQ ID NO 11
\<211\> LENGTH: 51
\<212\> TYPE: DNA
\<213\> ORGANISM: Artificial Sequence
\<220\> FEATURE:
\<223\> OTHER INFORMATION: K1 Heavy chain variable region CDR2

\<400\> SEQUENCE: 11

```
gagatttatc ctagaagtgg taatacttac tacaatgaga agttcaaggg c              51
```

\<210\> SEQ ID NO 12
\<211\> LENGTH: 10
\<212\> TYPE: PRT
\<213\> ORGANISM: Artificial Sequence
\<220\> FEATURE:
\<223\> OTHER INFORMATION: K1 Heavy chain variable region CDR3

\<400\> SEQUENCE: 12

```
Val Tyr Tyr Tyr Gly Ser Ser Tyr Gly Tyr
1               5                   10
```

\<210\> SEQ ID NO 13
\<211\> LENGTH: 30
\<212\> TYPE: DNA
\<213\> ORGANISM: Artificial Sequence
\<220\> FEATURE:
\<223\> OTHER INFORMATION: K1 Heavy chain variable region CDR3

\<400\> SEQUENCE: 13

```
gtttattact acggtagtag ctacggctac                                      30
```

\<210\> SEQ ID NO 14
\<211\> LENGTH: 16
\<212\> TYPE: PRT
\<213\> ORGANISM: Artificial Sequence
\<220\> FEATURE:
\<223\> OTHER INFORMATION: K1 Light chain variable region CDR1

\<400\> SEQUENCE: 14

```
Lys Ser Ser Gln Ser Leu Leu Asp Ser Asp Gly Lys Thr Tyr Leu Asn
1               5                   10                  15
```

\<210\> SEQ ID NO 15
\<211\> LENGTH: 48
\<212\> TYPE: DNA
\<213\> ORGANISM: Artificial Sequence
\<220\> FEATURE:
\<223\> OTHER INFORMATION: K1 Light chain variable region CDR1

\<400\> SEQUENCE: 15

```
aagtcaagtc agagcctctt agatagtgat ggaaagacat atttgaat                  48
```

```
<210> SEQ ID NO 16
<211> LENGTH: 7
<212> TYPE: PRT
<213> ORGANISM: Artificial Sequence
<220> FEATURE:
<223> OTHER INFORMATION: K1 Light chain variable region CDR2

<400> SEQUENCE: 16

Leu Val Ser Lys Leu Asp Ser
1               5

<210> SEQ ID NO 17
<211> LENGTH: 21
<212> TYPE: DNA
<213> ORGANISM: Artificial Sequence
<220> FEATURE:
<223> OTHER INFORMATION: K1 Light chain variable region CDR2

<400> SEQUENCE: 17
ctggtgtcta aactggactc t                                             21

<210> SEQ ID NO 18
<211> LENGTH: 9
<212> TYPE: PRT
<213> ORGANISM: Artificial Sequence
<220> FEATURE:
<223> OTHER INFORMATION: K1 Light chain variable region CDR3

<400> SEQUENCE: 18

Trp Gln Gly Thr His Phe Pro Arg Thr
1               5

<210> SEQ ID NO 19
<211> LENGTH: 27
<212> TYPE: DNA
<213> ORGANISM: Artificial Sequence
<220> FEATURE:
<223> OTHER INFORMATION: K1 Light chain variable region CDR3

<400> SEQUENCE: 19
tggcaagcta cacattttcc tcggacg                                       27

<210> SEQ ID NO 20
<211> LENGTH: 127
<212> TYPE: PRT
<213> ORGANISM: Artificial Sequence
<220> FEATURE:
<223> OTHER INFORMATION: K1 Heavy chain variable region

<400> SEQUENCE: 20

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Val Tyr Tyr Tyr Gly Ser Ser Tyr Gly Tyr Trp Gly Gln Gly
            100                 105                 110
```

```
Thr Thr Leu Thr Val Ser Ser Glu Ser Gln Ser Phe Pro Asn Val
        115                 120                 125
```

<210> SEQ ID NO 21
<211> LENGTH: 381
<212> TYPE: DNA
<213> ORGANISM: Artificial Sequence
<220> FEATURE:
<223> OTHER INFORMATION: K1 Heavy chain variable region

<400> SEQUENCE: 21

```
sargtmmagc tgsagcagtc wggagctgag ctggcgaggc ctggggcttc agtgaagctg    60
tcctgcaagg cttctggcta caccttcaca agctatggta taagctgggt gaagcagaga   120
actggacagg ccttgagtg gattggagag atttatccta gaagtggtaa tacttactac    180
aatgagaagt tcaagggcaa ggccacactg actgcagaca atcctccag cacagcgtac    240 atggagctcc gcagcctgac atctgaggac tctgcggtct atttctgtgc aagggtttat    300
tactacggta gtagctacgg ctactggggc caaggcacca ctctcacagt ctcctcagag    360
agtcagtcct ccccaaatgt c                                              381
```

<210> SEQ ID NO 22
<211> LENGTH: 121
<212> TYPE: PRT
<213> ORGANISM: Artificial Sequence
<220> FEATURE:
<223> OTHER INFORMATION: K1 Light chain variable region

<400> SEQUENCE: 22

```
Asp Ile Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

Arg Ala Asp Ala Ala Pro Thr Val Ser
        115                 120
```

<210> SEQ ID NO 23
<211> LENGTH: 363
<212> TYPE: DNA
<213> ORGANISM: Artificial Sequence
<220> FEATURE:
<223> OTHER INFORMATION: K1 Light chain variable region

<400> SEQUENCE: 23

```
gayattgtgm tcacacarwc tccactcact ttgtcggtta ccattggaca accagcctcc    60
atctcttgca gtcaagtca gagcctctta gatagtgatg aaagacata tttgaattgg     120 ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttcct   300
```

```
cggacgttcg gtggaggcac caagctggaa atcaaacggg ctgatgctgc accaactgta    360
tcc                                                                  363
```

<210> SEQ ID NO 24
<211> LENGTH: 35
<212> TYPE: DNA
<213> ORGANISM: Artificial Sequence
<220> FEATURE:
<223> OTHER INFORMATION: Mouse heavy chain FR1 region high degeneracy
      primer
<220> FEATURE:
<221> NAME/KEY: misc_feature
<222> LOCATION: (18)..(18)
<223> OTHER INFORMATION: n is a, c, g, or t
<400> SEQUENCE: 24

```
cttccggaat tcsargtnma gctgsagsag tcwgg                                35
```

<210> SEQ ID NO 25
<211> LENGTH: 33
<212> TYPE: DNA
<213> ORGANISM: Artificial Sequence
<220> FEATURE:
<223> OTHER INFORMATION: Mouse IgM heavy chain constant region primer
<400> SEQUENCE: 25

```
ggaagatctg acatttggga aggactgact ctc                                  33
```

<210> SEQ ID NO 26
<211> LENGTH: 30
<212> TYPE: DNA
<213> ORGANISM: Artificial Sequence
<220> FEATURE:
<223> OTHER INFORMATION: Mouse kappa chain constant region primer
<400> SEQUENCE: 26

```
ggtgcatgcg gatacagttg gtgcagcatc                                      30
```

<210> SEQ ID NO 27
<211> LENGTH: 32
<212> TYPE: DNA
<213> ORGANISM: Artificial Sequence
<220> FEATURE:
<223> OTHER INFORMATION: Mouse kappa chain FR1 region universal
      degenerate primer <400> SEQUENCE: 27

```
gggagctcga yattgtgmts acmcarwctm ca                                   32
```

<210> SEQ ID NO 28
<211> LENGTH: 9
<212> TYPE: PRT
<213> ORGANISM: Artificial Sequence
<220> FEATURE:
<223> OTHER INFORMATION: Synthetic
<400> SEQUENCE: 28

Cys Arg Met Ser Arg Arg Ser Asn Cys
 1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic

```
<400> SEQUENCE: 29

Cys Met Arg Asn Arg Pro Lys Arg Cys
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Cys Arg Arg Arg Leu Asn Arg Thr Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Cys Arg Met Arg Ile Arg Arg Asn Cys
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Cys His Pro His Pro Arg Pro Arg Cys
1               5

<210> SEQ ID NO 33
<211> LENGTH: 16
<212> TYPE: PRT
<213> ORGANISM: Artificial Sequence
<220> FEATURE:
<223> OTHER INFORMATION: Synthetic

<400> SEQUENCE: 33

Arg Leu Lys Glu Asp Thr Gln Val Ala Asp Val Thr Thr Ser Arg Cys
1               5                   10                  15

<210> SEQ ID NO 34
<211> LENGTH: 23
<212> TYPE: PRT
<213> ORGANISM: Artificial Sequence
<220> FEATURE:
<223> OTHER INFORMATION: Synthetic

<400> SEQUENCE: 34

Arg Ala Lys Met Thr Pro Gly Cys Glu Ala Glu Ala Glu Ala
1               5                   10                  15

Leu Cys Phe Phe Ile Lys Gln
            20

<210> SEQ ID NO 35
<211> LENGTH: 24
<212> TYPE: PRT
<213> ORGANISM: Artificial Sequence
<220> FEATURE:
<223> OTHER INFORMATION: Synthetic
```

```
<400> SEQUENCE: 35

Lys Leu Gly Met Leu Ser Pro Asp Gly Thr Cys Arg Ser Phe Asp Asp
1               5                   10                  15

Ser Gly Ser Gly Tyr Cys Arg Ser
            20

<210> SEQ ID NO 36
<211> LENGTH: 27
<212> TYPE: PRT
<213> ORGANISM: Artificial Sequence
<220> FEATURE:
<223> OTHER INFORMATION: Synthetic

<400> SEQUENCE: 36

Arg Gly Gln Cys Ile Lys Asp Ala His Leu Pro Pro Gly Ser Met Ala
1               5                   10                  15

Ala Val Gly Leu Ser Trp Glu Glu Cys Lys Gln
            20                  25
```